United States Patent [19]
Gentile et al.

[11] Patent Number: 5,955,095
[45] Date of Patent: Sep. 21, 1999

[54] MICROPOROUS MACROCAPSULES

[75] Inventors: Frank T. Gentile, Warwick; Tyrone Hazlett, Coventry, both of R.I.; Patrick A. Tresco, Sandy, Utah; Thomas Flanagan, Barrington, R.I.; Edward J. Doherty, Mansfield, Mass.; David Rein, Providence, R.I.; Laura M. Holland, Ambler, Pa.

[73] Assignee: Brown University Research Foundation, Providence, R.I.

[21] Appl. No.: 08/436,281

[22] PCT Filed: Nov. 16, 1993

[86] PCT No.: PCT/US93/11232

§ 371 Date: Aug. 14, 1995

§ 102(e) Date: Aug. 14, 1995

[87] PCT Pub. No.: WO94/10950

PCT Pub. Date: May 26, 1994

Related U.S. Application Data

[63] Continuation-in-part of application No. PCT/US92/03327, Apr. 22, 1992.

[51] Int. Cl.[6] .............................. A61K 9/48; A61F 13/00
[52] U.S. Cl. .......................... 424/422; 424/463; 424/520
[58] Field of Search .................................. 424/422, 451, 424/462, 424, 520

[56] References Cited

U.S. PATENT DOCUMENTS

| | | | |
|---|---|---|---|
| 4,353,888 | 10/1982 | Sefton | 424/25 |
| 4,803,168 | 2/1989 | Jarvis, Jr. | 435/240.22 |
| 4,806,355 | 2/1989 | Goosen et al. | 424/424 |
| 5,015,476 | 5/1991 | Cochrum et al. | 424/423 |
| 5,106,627 | 4/1992 | Aebischer et al. | 424/424 |
| 5,182,111 | 1/1993 | Aebischer et al. | 424/424 |

OTHER PUBLICATIONS

Stanier, et al., "The Bacterial Virus" *General Microbiology* 373–374 (1976).

Freshney, "Virus Preparation and Assay" *Culture of Animal Cells: A Manual of Basic Technique* (A John Wiley & Sons, Inc.: New York) pp. 402–403.

*Primary Examiner*—Sally Gardner-Lane
*Attorney, Agent, or Firm*—Leon R. Yankwich; Ivor R. Elrifi

[57] ABSTRACT

Microporous macrocapsules are disclosed which are useful as implantation devices for cell therapy. The macrocapsule comprises living cells that secrete biological substance that are therapeutically useful and that are released from the macrocapsule to the site of implantation. The capsules can have selected permeability characteristics based upon their particular usage and desired viral retentivity characteristics.

19 Claims, 2 Drawing Sheets

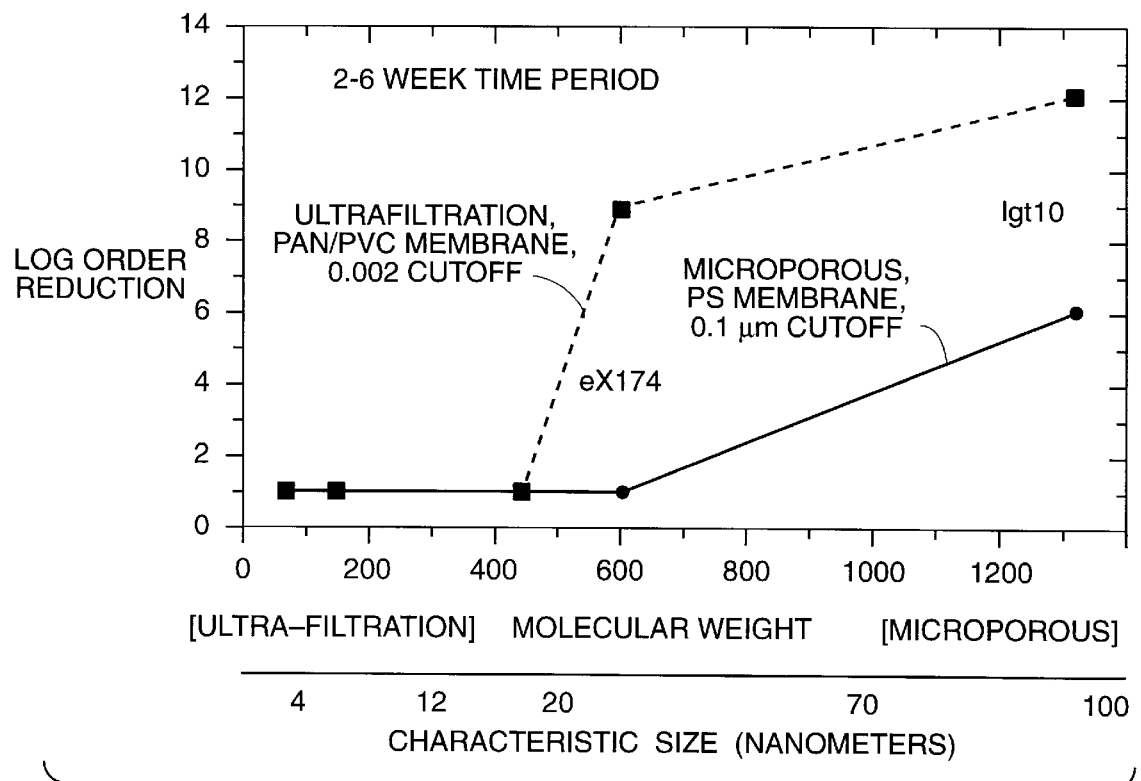
FIG._1
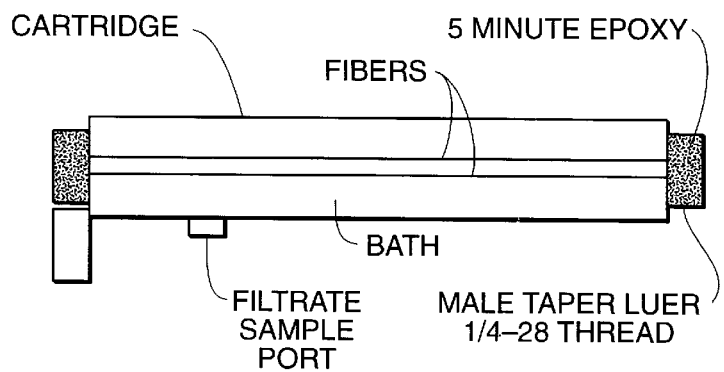
FIG._2

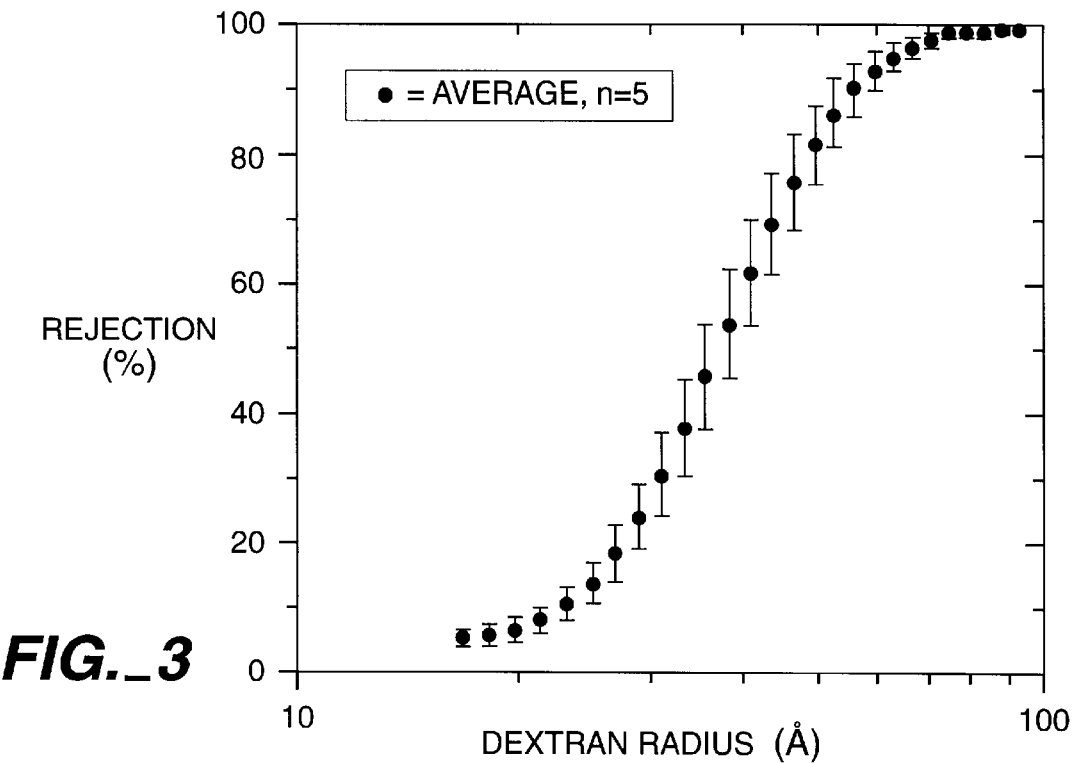
FIG._3
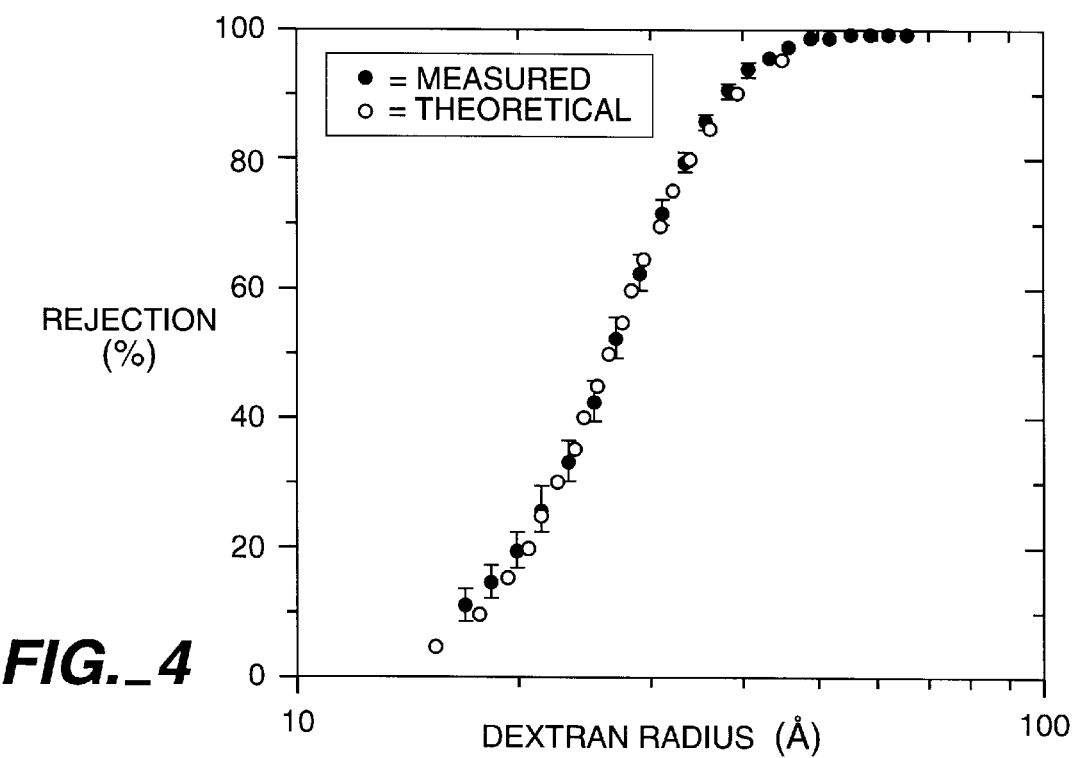
FIG._4

MICROPOROUS MACROCAPSULES

CROSS-REFERENCES TO RELATED APPLICATIONS

This application is a national stage filing under 35USC371 of PCT/US93/11232 which claims priority to U.S. Ser. No. 07/975,354 now abandoned, which is a continuation-in-part of copending PCT application U.S. Pat. No. 92103327, filed Apr. 22, 1992, which claims priority to U.S. Ser. No. 07/692,403, filed Apr. 25, 1991. The contents of the related applications are hereby expressly incorporated by reference.

BACKGROUND OF THE INVENTION

The present invention is directed to macrocapsules and their use as implantation and retrieval devices for cells.

The methods of implanting living cells and or tissue into the body to provide therapeutically useful substances (cell therapy) is currently the focus of a number of research efforts. Among others, therapeutic applications for cell therapy have been suggested in the areas of diabetes and neural degenerative diseases such as Alzheimer's Disease, Parkinson's Disease and epilepsy. Additionally, cells have also been shown to have great therapeutic potential for the removal of detrimental substances from the body. For example, hepatocytes have been implanted for the treatment of high cholesterol levels as shown by Wang et al., *Transplantation Proceedings*, 23:894–895 (1991).

In one form of cell therapy, the cells that are implanted into the patient have been genetically modified (transduced) in vitro with exogenous genetic material so as to enable the cells to produce a desired biological substance that is useful as a therapeutic agent. There are variety of mechanisms for transducing cells. Retroviral vectors have been of interest due to the ability of some vectors to transduce a very high percentage of target cells. Replication of target cells is necessary for proviral integration to occur using these vectors. In theory, cells transduced with retroviruses are not able to spread virus to other cells. However, several safety issues surround the use of these systems. Risks include the potential during production of the retroviral vector preparations for contamination with infectious viruses or pathogens (Cornetta, *Human Gene Therapy* Vol 2:5–14, 1991).

Adenoviruses are also used as gene transfer vectors. They are double stranded DNA viruses capable of infecting post-mitotic cells, and their successful transfection of host cells can result in the expression of large amounts of gene product. Adenoviruses are a minor pathogen in humans and are not normally associated with malignancies. While the adenovirus vector generally remains episomal and does not undergo replication, studies have shown that gene expression can persist for a significant period, opening up the possibility that the vectors are at least replication-competent.

While present cell therapy methods show great therapeutic potential, they have several limitations. The injection of cells into a patient can create a severe immune reaction. An immune reaction to a first injection of cells will most likely preclude a second injection, thus limiting the benefit which can be gained from such treatment. Some candidate cell types may shed virus particles which could be detrimental to the host and therefore may not be considered suitable for implantation. In the case of cells that have been genetically modified to produce a desired biological substance using viral techniques, the cells may harbor viral particles, thus allowing the possibility of infecting a patient's cells. Another disadvantage with the current cell therapy methods is that many cells that might be suitable for such therapies are known to migrate in situ, (e.g. glial cells). The inability to retain implanted cells in a fixed location may make them unsuitable as therapeutic agents. Likewise, cells which are autologous or even allogeneic to the host may continue to divide unchecked and produce tumors.

Current methods of cell therapy do not readily allow termination of, or adjustments to, the cell therapy protocol once the cells are implanted. This is because cells implanted into a patient's body are not well isolated from the patient's own tissue and thus cannot be readily retrieved or manipulated. This creates a real fear when the cells have been genetically modified using retroviral particles because implanted cells could migrate in situ and potentially result in proviral integration into the host germ line cells, thus passing the provirus onto offspring.

There are a number of specific circumstances where it may be critical to terminate or remove implanted therapeutic cells. These include:

1. One or more of the implanted cells has become oncogenic or tumor forming, or has induced an adverse immune reaction.
2. A dose adjustment may require a reduction in the number of implanted cells at specific times.
3. Genetically engineered cell populations may have a small number of cells with improper incorporation of genetic material leading to detrimental effects.
4. The therapy may have a defined end point (e.g. growth hormone treatment) at which the point the continued presence of the therapeutic cells is unwanted or detrimental.
5. Genetically modified cells may develop an adverse response to concurrently administered pharmacological agents.
6. The development of an improved therapeutic option may warrant a change in therapy requiring removal of the transplanted cells.

Incorporation of inducible suicide genes into cells for implantation has been suggested as a potential means to terminate cell therapy i.e. by killing the implanted cells. One disadvantage of this approach, however, is that since cell division is a stochastic process, there is always a chance that the suicide mechanism in one or a few cells might become inactivated. Undesirable effects could be produced even if only one of the cells continued to divide. This approach also may have undesirable results caused by the dumping of secretory products such as growth factors or proteases or the release of viruses, etc., due to the large scale destruction of implanted cells.

Cell encapsulation methods have been used to isolate cells while allowing the release of desired biological materials. Two techniques have been used, microencapsulation and macroencapsulation. Typically, in microencapsulation, the cells are sequestered in a small permselective spherical container, whereas in macroencapsulation the cells are entrapped in a larger non-spherical membrane.

Lim, U.S. Pat. Nos. 4,409,331 and 4,352,883, discloses the use of microencapsulation methods to produce biological materials generated by cells in vitro, wherein the capsules have varying permeabilities depending upon the biological materials of interest being produced. Wu et al, *Int. J. Pancreatology*, 3:91–100 (1988), disclose the transplantation of insulin-producing, microencapsulated pancreatic islets into diabetic rats. Aebischer et al., *Biomaterials*, 12:50–55 (1991), disclose the macroencapsulation of dopamine-secreting cells.

Various polymeric materials have been used in the art for filtering viruses from liquids. Anazawa et al. (U.S. Pat. No. 5,236,588) teach an ultrafiltration membrane prepared by irradiating a monomer to produce a membrane having communicating pores. Allegrezza U.S. Pat. No. 5,096,637) reports an asymmetric composite ultrafiltration membrane for isolating viruses from protein containing solutions. DiLeo (U.S. Pat. No. 5,017,292) teaches asymmetric skinned membranes comprising a porous substrate, an ultrafiltration surface skin and an intermediate zone free of voids which form a break in the skin and which cause fluid to communicate directly with the porous substrate. The membranes are used for isolating viruses from protein containing solutions. U.S. Pat. Nos. 4,808,315 and 4,857,196 teach a hydrophilic hollow fiber membrane for removing virus from a protein containing solution.

None of the above references describe virally retentive, permselective, biocompatible membranes that can be implanted into a patient for cell-therapy purposes. There are many situations where it would be useful to provide cell therapy for the in vivo delivery of biological materials, while substantially preventing release of detrimental viruses that may be shed from the encapsulated cells. There are also many situations where easy termination of cell therapy treatment would be desirable. However, effective means for such treatments are lacking in the art of cell therapy.

Accordingly, it is an object of the present invention to provide methods for cell therapy that can be easily terminated at a desired time by providing a method for the retrieval of implanted cells.

It is another object of the present invention to provide macrocapsules to encapsulate cells wherein the capsules have selected permeability characteristics based upon their particular usage and desired viral retentivity characteristics.

It is another object of the present invention to provide methods for testing the viral retentivity of macrocapsules.

These and other objects and features of the invention will be apparent to those skilled in the art from the following detailed description and appended claims.

None of the foregoing references is believed to disclose the present invention as claimed and is not presumed to be prior art. The references are offered for the purpose of background information.

SUMMARY OF THE INVENTION

An implantable permselective macrocapsule is described for use in cell therapy. The macrocapsule comprises a core comprising living cells that are capable of secreting a selected biologically active product or of providing a selected biological function and an external jacket which surrounds the core. The jacket comprises a biocompatible material that is substantially free of the encapsulated cells and has a nominal molecular weight cutoff sufficient to retain the cells within said macrocapsule. In some embodiments the nominal molecular weight cutoff of the macrocapsule is below the molecular weight of detrimental viruses which may be shed from said living cells.

A method for determining the viral retentivity of an external jacket of an implantable permselective macrocapsule is also described wherein the external jacket comprises a hollow fiber and virus is loaded into the hollow fiber. The ends of the hollow fiber are then sealed and the fiber is placed into a bath solution. After a time interval, the bath solution is innoculated onto a lawn of bacteria susceptible to the virus and viral retentivity is calculated based on the number of plaques formed.

BRIEF DESCRIPTION OF THE DRAWINGS

FIG. 1 shows the log-order reduction in release of phage from the microporous macrocapsules.

FIG. 2 shows the testing cartridge used to measure the viral retentivity of the microporous macrocapsules.

FIGS. 3 and 4 show the percent rejection of various sized dextrans from the microporous macrocapsules.

DETAILED DESCRIPTION OF THE INVENTION

The instant invention provides permselective, biocompatible macroencapsulation devices and methods of using them for restraining cells, retaining certain detrimental viruses shed from restrained cells or preventing the entry of detrimental viruses from host tissue through the encapsulation device. The macrocapsules also allow for the efficient termination of cell therapy regimes. The inventive methods all rely on permselective macroencapsulation devices which, depending upon the nature of the cells to be implanted and the site of implantation, may or may not have immunoisolatory characteristics. Thus in some instances, the cells are capable of producing a desired function without the need of a physical barrier between themselves and the immune system of the recipient. Such cells are many of the same cells believed useful for classic unencapsulated cell therapy.

The macrocapsules of the present invention are biocompatible. The term "biocompatible" as used herein refers collectively to both the intact macrocapsule and its contents. Specifically, it refers to the capability of the implanted intact macrocapsule and its contents to avoid detrimental effects of the body's various protective systems, such as the immune system or foreign body fibrotic response, and remain functional for a significant period of time. In addition, "biocompatible" also implies that no specific undesirable cytotoxic or systemic effects are caused by the vehicle and its contents such as would interfere with the desired functioning of the vehicle or its contents.

The macrocapsules are also "permselective", and they can have their permeability characteristics tailored for their specific usage. For example, macrocapsules that are used to encapsulate xenogeneic cells, which may harbor detrimental viruses, may be designed to minimize the release of the viruses. The methods of the present invention allow one to know prior to the implantation of a particular macrocapsule, its viral retentivity/retardation characteristics. Viral retentivity (how much the membrane retards viral transport) can be determined by calculating $D_{membrane}/D_{water}$, where D is the diffusion coefficient of the substance through the membrane. This compares the resistance of transport through the membrane with that of an equivalent distance of water. For viruses of the 18–120 nm sizes, $D_{water}$ is $2.4 \times 10^{-7}$ cm$^2$/sec to $3.8 \times 10^{-8}$ cm$^2$/sec. The diffusion coefficients of various viruses through membranes were measured based upon the data initially and at six weeks. The diffusion coefficient is a measure of resistance to transport through the membrane and is given by the equation:

$$J = D(\Delta C)/(\Delta X)$$

where J is the flux through the membrane, $\Delta C$ is the concentration difference between the inside and the outside of the membrane, and $\Delta X$ is the membrane wall thickness. D is a constant and is independent of concentration. It is a proportionality constant between $\Delta C$ and the resulting flux, J. The viral retentivity of a membrane is preferably less than about 0.5, more, preferably less than 0.1, and most preferably less than about $10^{-2}$. Preferably the membrane, once implanted into the patient, will maintain its viral retentivity/retardation properties at least 1 week, preferably at least 2 weeks, and more preferably at least 6 weeks. It is most preferable for the membrane to retain a given viral retentivity/retardation value for the duration of the therapy.

The permselective characteristic of a macrocapsule can also be defined in terms of its molecular weight cutoff. The term "molecular weight cutoff" (MWCO) refers to the size or molecular weight of particles which are retained by a particular membrane under convective or pressure driven conditions. Since semipermeable membranes generally have a Gaussian distribution of pore sizes, the term MWCO as used herein refers to the size of a marker molecule when tested with a specific membrane, 90% of which is retained by the membrane under the test condition. Specifically, while the majority of pores in a membrane may be large enough to retain a given particle, some pores may exist which are large enough for the molecule to pass through. Thus, the MWCO of a given membrane is not an absolute and may differ somewhat when measured using different tests. While particles of a particular size, if large enough, may be completely retained for a given period of time, there is a range of particle sizes where a portion of particles will be retained and a portion will be released. If, for example, 60% of particles having a molecular weight of about 50 kD are retained by a given membrane, then a greater percentage of particles that are larger than 50 kD will be retained by the same membrane given the same time period. The term "nominal MWCO" (nMWCO) refers to the size of particles retained by the macrocapsule at 90% levels. Thus, for example, if 100 kD particles are retained by a membrane at 90% levels, the nMWCO of the macrocapsule is 100 kD.

There are several different methods for measuring nMWCO, which can give different results. Tests may be diffusive or convective. Convective methods measure transmembrane diffusion under pressure. The convective nMWCO is a good indicator of how quickly molecules will passively diffuse from the membrane. When testing nMWCO, it is important to realize that the shape and nature of the molecule used in testing may influence the measured values. Thus, when comparing data from various sources, it is important to consider the test method employed to obtain the values.

The macrocapsules can be designed to retain cells that have been genetically modified with viruses to secrete a desired biological substance that is useful as a therapeutic agent. The nMWCO is selected so that the biological substance is substantially released from the capsule, but residual viral particles, which may be harbored by the modified cells, is substantially retained. The phrase "genetically modified with virus" includes any standard method used in the art to introduce exogenous DNA by viral vectors (retrovirus, modified herpes viral, herpes-viral, adenovirus, adeno-associated virus, and the like) to the cells that are to be encapsulated.

In some embodiments, the macrocapsules of the invention will be permeable to substances of greater molecular weight than the C1q component of complement which has a molecular weight of about 440 kD. Thus, these embodiments will be substantially non-immunoisolatory. Such capsules will generally be implanted at immuno-privileged sites, such as the brain. The capsules have the primary purpose of serving as cell retrieval devices. The relatively high MWCOs of such devices will enable relatively large therapeutically useful agents to be released from the cells and delivered to the site of implantation. Macrocapsules that serve primarily as cell retrieval devices may have MWCOs in the 1,000–3,000 kD range. The relatively high molecular weight cutoffs (MWCOs) of the macrocapsules can be achieved by methods standard in the art including those taught by Strathmann in "Production of Microporous Media by Phase Inversion Processes," *Materials Science of Synthetic Membranes*, ACS Symposium Series 269, American Chemical Society, Washington D.C. (1985). Additionally, various methods for altering the MWCO of the macrocapsules are described below.

The permselective macrocapsules can be manufactured by the same methods and using the same materials disclosed in copending PCT application U.S. Pat. No. 92/03327. Briefly, the capsule is comprised of (a) a core which contains isolated cells, either suspended in a liquid medium or immobilized within a hydrogel matrix, and (b) a biocompatible surrounding or peripheral region ("jacket") of permselective matrix or membrane which is substantially free of the isolated cells.

The core of the macrocapsule is constructed to provide a suitable local environment for the particular cells isolated therein. In some embodiments, the core comprises a liquid medium sufficient to maintain the cells. Liquid cores are particularly suitable for maintaining transformed cells, such as PC12 cells. In other embodiments, the core comprises a hydrogel matrix which immobilizes and distributes the cells, thereby reducing the formation of dense cellular agglomerations.

Cores made of a hydrogel matrix are particularly suitable for maintaining primary cells which tend to form agglomerates, such as the cells in islets of Langerhans, or adrenal chromaffin cells. Optionally, the core of the instant vehicle can contain substances which support or promote the function of the isolated cells. These substances include natural or synthetic nutrient sources, extracellular matrix (ECM) components, growth factors or growth regulatory substances, or a population of feeder or accessory cells.

The jacket of the macrocapsule is made of a material which may be the same as that of the core or may be different. In either case, the material used results in a surrounding or peripheral region which is permselective and biocompatible. The biocompatibility of the jacket means that it does not elicit a detrimental immune response sufficient to result in rejection of the implanted macrocapsule or to render it inoperable. It also means that the jacket does not elicit unfavorable tissue responses. In addition, the external surface can be selected or designed in such a manner that it is particularly suitable for implantation at the selected site. For example, the external surface can be smooth, stippled or rough, depending on whether attachment by cells of the surrounding tissue is desirable. The shape or configuration can also be selected or designed to be particularly appropriate for the implantation site chosen. Typically the jacket will comprise permselective membranes which have been formed into hollow fibers or flat sheets. A hollow fiber membrane is an annulus consisting of an inner cylindrical surface, a wall structure for support, and an outer cylinder surface. One or both of the surfaces can be selective for molecules of varied molecular weight. A flatsheet is a planar composition of a hollow fiber.

The surrounding or peripheral region of the jacket can be made of a hydrogel matrix or of a different material, such as a thermoplastic membrane or hollow fiber. It can also be made of a matrix-membrane composite, such that a permselective thermoplastic membrane having matrix-filled pores, such as hydrogel filled pores, is formed.

Suitably, the external jacket may be formed of a thermoplastic material known to be biocompatible, such as the ones described herein. In addition, other jackets which have been used in the microcapsule field may also be used herein, such as alginate, suitably cross-linked with a multivalent ion such as calcium.

The jacket may be directly cross-linked to the core matrix, eliminating the need for an intermediate linking layer such as poly-L-lysine (PLL). The elimination of an intermediate PLL layer is advantageous in that PLL is believed to be fibrogenic. Also, the jacket in this device can be controlled for permselectivity better than those made with PLL.

The macrocapsule can be formed by coextrusion or in a step-wise fashion. Techniques for coextrusion, which can be used to form the macrocapsules of the present invention, are taught in U.S. Pat. No. 5,158,881. With the coextrusion method, the macrocapsules are formed by coextruding, from a nested-bore extrusion nozzle, materials which form the core and surrounding or peripheral regions, under conditions sufficient to gel, harden, or cast the matrix or membrane precursor(s) of the surrounding or peripheral region (and of the core region). A particular advantage of this coextrusion embodiment is that the cells in the core are isolated from the moment of formation of the vehicle, ensuring that the core materials do not become contaminated or adulterated during handling of the vehicle prior to implantation. A further advantage of the coextrusion process is that it ensures that the surrounding or peripheral region is free of cells and other core materials.

The macrocapsule can also be formed step-wise. For example, if the capsule being made includes a hydrogel core containing the isolated cells, the core can be formed initially, and the surrounding or peripheral matrix or membrane can be assembled or applied subsequently. Conversely, the surrounding or peripheral matrix or membrane can be preformed, and then filled with the preformed isolated-cell containing core material or with materials which will form the core (i.e., core precursor materials). The capsule is sealed in such a manner that the core materials are completely enclosed. If a core precursor material is used, the vehicle is then exposed to conditions which result in formation of the core.

The surrounding or peripheral region is produced in such a manner that it has pores or voids of a predetermined range of sizes; as a result, the vehicle is permselective. The permeability and biocompatibility characteristics of the surrounding or peripheral region are determined by both the matrix or membrane precursor materials used, and the conditions under which the matrix or membrane is formed.

The molecular weight cutoff (MWCO) selected for a particular vehicle will be determined by the molecular size of the largest substance to be allowed to pass into and/or out of the vehicle. In some instances, where viral release is not a concern, the pores of the macrocapsule will be as large as possible while still retaining cells, about from 0.1–10 $\mu$m, depending on the type of cell encapsulated.

Hollow fiber membranes can be prepared in a wide range of MWCOs for the purposes of exclusion or delivery of various biological agents while preventing significant passage either into or out of the capsule of detrimental viruses. Alteration of the MWCO of the macrocapsule can be accomplished by a variety of methods. The basic methodology of alteration of membrane cutoff is to alter the phase separation properties of a given set of membrane casting solutions and coagulation baths. The thermodynamics of phase separation for each material/solvent combination is different. In general, the longer it takes for the phase inversion process to take place, the larger the pore-size of the resulting membrane. The particular membrane material selected will affect the MWCO. Material/solvent systems such as poly(sulfone)/N-methyl pyrrolidone (NMP) and poly(vinylidene difluoride) (PVDF)/tetrahydrofuran (THF) are more easily made into higher MWCO membranes, due to the strength of the polymer/solvent/nonsolvent interactions, than materials such as poly(acrylonitrile) (PAN)/dimethyl sulfoxide (DMSO). Permeability properties of membranes can be selected by choosing appropriate material systems. For example, using a system where the polymer is somewhat soluble in the precipitating liquid will greatly slow down the phase inversion process.

The addition of a low molecular weight additive to the membrane casting solution in which the main membrane polymer is not soluble will also affect the MWCO of the membrane (Cabasso, 1976). Low molecular weight, non-soluble additives make the casting solution less stable. Such solutions can phase invert much faster resulting in potential lower MWCO membranes. Conversely, higher molecular weight additives can result in slower phase separation which will cause relatively large pores to form. An example of this is when poly(acrylonitrile-co-vinyl chloride) (PAN/PVC) is blended with high molecular weight polyethylene oxide (PEO) (MW>100 kD). Also, higher molecular weight or macroscopic additives will perhaps diffuse away from the membrane matrix and leave behind large pores.

The resulting molecular weight of a membrane can also be altered by the addition of a membrane polymer solvent to both the inner bore and outer coagulation solutions. Addition of solvent greatly slows down the precipitation, which can result in much higher cutoff membranes.

Changing the temperature during the membrane formation process can also affect the MWCO. This method of altering MWCO is usually used in combination with solvent or non-solvent additions because temperature change alone does not always alter MWCO. For example, solutions of polysulfone, PEG-200 and (NMP) can be made into fibers of differing MWCOs by adjusting the temperature of the coagulation bath. This system combination is termed a "lower critical solution temperature system" (LCST) in which the stability of the solution goes down with increasing temperature. Thus, higher temperatures give rise to higher MWCOs. Changing the temperature of the casting and the coagulation solutions during the course of membrane formation will also alter the MWCO. Combinations of any of the above techniques can also be used to alter MWCO. For example, temperature change in combination with the addition of a high or low molecular weight additive can be used to affect MWCO.

Because of the moderate to high MWCO characteristics of some embodiments of the present invention, the macrocapsules will have high permeabilities and resultant enhanced diffusional characteristics across the outer device wall. The improved transport properties mean the capsules will support higher level densities of viable cells than immunoisolatory capsules, which have lower MWCOs in order to prevent immunological rejection from the transplant recipient. Higher cell densities may allow the use of smaller devices as compared to immunoisolatory capsules since they provide more therapeutic substance per unit volume. By the term "immunoisolatory capsule" it is meant that the permselectivity of the capsule is such that it protects cells in its core from the immune system of the individual in whom the vehicle is implanted. It does so by preventing harmful substances of the individual's body from entering the core of the vehicle, by minimizing contact between the individual and inflammatory, antigenic, or otherwise harmful materials which may be present in the core and by providing a spatial barrier sufficient to prevent immunological contact between the isolated cells and the individual's immune system.

For ease of retrieval, the macrocapsules will generally have one or more tethers to allow location and grasping of the device without damage to it. Additionally, the tether can be used to find the implanted macrocapsule when it is desirous to terminate therapy. Tethers are made according to the methods of Aebischer et al. in copending PCT application U.S. Pat. No. 92/05369. The macrocapsules can also be made to contain substances that enhance imaging to aid in the implantation of the device to the target site.

When the permselectivity of the macrocapsules is such that they are substantially non-immunoisolatory, the cells to be encapsulated should be compatible with the desired therapy or function. They will be cells that survive, with or without immunoisolation, long enough to have therapeutic value to the recipient. In general, choice of cells for specific functions, methods to insure implant survival, and various other considerations concerning cell viability in cell therapy situations are the same as those outlined by Gage et al., U.S. Pat. No. 5,082,670.

In some instances, it may be possible to provide cell therapy using the transplant recipient's own cells (e.g. in the case of tumor, endothelial or epithelial biopsies etc.). Cells that are syngeneic to that of the recipient may also be used. In these situations, the lack of immunoisolation provided by the macrocapsule is of little concern. However, when xenogeneic and/or allogeneic cells are used, immunosuppressive techniques may be required. Local immunosuppression methods are disclosed by Gruber, *Transplantation* 54:1–11 (1992), and by Rossini, U.S. Pat. No. 5,026,365. General reviews and citations for the use of recombinant methods to reduce antigenicity of donor cells are disclosed by Gruber (supra). Exemplary approaches to the reduction of immunogenicity of transplants by cell surface modification are disclosed by Faustman WO 92/04033 (1992).

Weiss, WO 93/14767, discloses methods of making antigen depleted cells from target cells. Sims, WO93/02188, discloses genetically modified universal donor cells.

When the cells to be encapsulated are xenogeneic to the recipient, the need for immunosuppression is the greatest. Generally some method of reducing or eliminating the immune response to the encapsulated cells needs be employed. Thus recipients will often be immunosuppressed, either through the use of immunosuppressive drugs such as cyclosporin, or through local immunosuppression strategies employing locally applied immunosuppressants. Alternatively the immunogenicity of the cells may be reduced by preparing cells from a donor with reduced antigenicity, such as transgenic animals which have altered or deleted MHC antigens.

When cells that are allogeneic to that of the recipient are used, most often tissue typing will be used in an effort to most closely match the histocompatibility type of the recipient.

An approach to insuring the viability of implanted cells as an alternative to such methods as immunomodulation, cell surface modification, and general and local immunosuppression, is the placement of cells within an immunoisolatory device prior to placement in the permselective macrocapsule. Suitable immunoisolatory devices would include microspheres or alginate noodles. Alginate has been demonstrated to be a useful immunoisolant as long as it contains a cell free region around the perimeter.

For cell therapy purposes, the macrocapsules of the present invention additionally make useful as therapeutic agents some cells which are currently not useful for unencapsulated cell therapy because such cells have specific disadvantageous properties such as the shedding of detrimental viruses or unwanted migratory characteristics.

In cell therapy methods, it is desirable to protect the host from viruses which may be carried by donor cells. Oftentimes, xenogeneic cells are used. While xenogeneic tissue is preferably sourced from herds of animals having carefully controlled heredity and diet, viral contamination is still possible. While most animal viruses will not be transmitted to humans, there are a number of zoonotic diseases which can be transmitted from animals to humans by a virus. For example, viruses which can be transmitted from cattle to humans include Bovine Diarrhea Virus, Infectious Bovine Rhinotracheitis Virus, Para-Influenza 3 Virus, Bovine Adeno Virus, Bovine Parvo Virus, Bovine Reovirus. The permeability of the encapsulation devices can be tailored so that the host is protected from these and other adventitious agents which could be released from xenogeneic cells.

Even in the case of allografts, tissue may contain pathogens. While it is possible to screen for many detrimental agents, it is not possible to do so for all. For example, the diagnosis of HIV-free tissue may not be guaranteed because antibodies to the virus are generally not present until several weeks after infection. Such agents are transmissible and use of macrocapsules that retard the transport of viruses add an additional measure of safety.

It may also be desirable to provide protection to the encapsulated tissue from viral attacks from an infected host. While there are many diseases which are clearly viral in origin, there are others, such as multiple sclerosis, amyotrophic lateral sclerosis and schizophrenia, where viral etiologies have been hypothesized. By having healthy cells encapsulated within a membrane which retards viral transmission, an infected host may be treated by cell therapy.

Table 1 lists various diseases and conditions for which the permselective macroencapsulation cell therapy methods of the present invention may be useful, and the corresponding therapeutic substances that are released from the encapsulated cells.

TABLE 1

| Disease/Condition | Therapeutic Substance Deliverable by Genetically Engineered Cells |
| --- | --- |
| Leukemia | α-interferon |
| Kaposi's Sarcoma | |
| Hepatitis B | |
| Hepatitis C | β-interferon |
| M.S. | |
| Renal carcinoma | γ-interferon |
| Chronic granulomatosis | |
| Congenital leukopenia | granulocyte colony stimulatory factor |
| Hemophilia | Factor VIII, Factor IX |
| B Cell lymphoma | Idiotypic antibodies |
| Autoimmune disease | antibody-secreting cells |
| Arthritis | Il1-RA |
| Gaucher's disease | Glucocerebrosidase |
| Elevated cholesterol | macrophage colony stimulating factor |
| Tumors | tumor necrosis factor |
| Angioplasty | tPA |
| Growth hormone deficiency | growth hormone |
| Nerve degeneration | nerve growth factors |
| Bone repair | bone morphogenic peptide |

Because viruses exist in a wide variety of shapes and sizes, various assays may be used to determine whether a given membrane will have the desired properties relative to a given virus. The present invention provides a method to test fibers for their properties relative to viruses so that their viral release rate may be approximated upon implantation. This method includes plaquing techniques which are known to be particularly sensitive to viruses. In many cases, the particular virus of interest may be tested directly by loading a given concentration of virus into the lumen of a fiber, securely sealing the ends, and placing the fiber in a bath solution. The bath solution can then be tested at desired time intervals and assayed for viruses using standard plaquing procedures [Davis, B., *Microbiology: including Immunology and Molecular Genetics*, 3rd ed., Harper & Row (1980)]. In cases where it may be undesirable to test the virus of interest directly (e.g. pathogenic viruses) a model of the virus of interest can be used. Bacteriophages of similar dimensions of the virus of interest serve as useful models due to their viral nature. A variety of phages are available from the ATCC, and are also listed in *Molecular Cloning: A Laboratory Manual* (Sambrook, J. et al., Cold Spring Harbor Laboratory Press, 1989). A single virus may infect a target bacterium. The virus will replicate and be released to surrounding bacteria. Thus very low levels of virus may be identified by plaque formation on a lawn of bacteria.

Table 2 gives the sizes of some representative animal viruses. They range from 18–26 nm for the parvoviruses to 150–300 nm for the paramyxo (parainfluenza) viruses.

TABLE 2

Sizes of Representative Animal Viruses

| Virus Family | Virus | Diameter (nm) |
| --- | --- | --- |
| Parvoviridae (DNA) | Parvo | 18–26 |
| Adenoviridae (DNA) | Adeno | 70–90 |
| Picornaviridae (RNA) | Rhino | 24–30 |
| Reoviridae (RNA) | Reo | 75 |
| Orthomyxoviridae (RNA) | Influenza | 80–120 |
| Paramyxoviridae (RNA) | Paramyxo (para influenza) | 150–300 |
| Retroviridae | oncovirus (Type C, B, D) | ~100 |

Table 3 gives the molecular weight, Stokes radius, and diffusivity of various markers and viruses.

TABLE 3

Molecular Weight, Stokes Radius, and Diffusivity of Various Markers

| Marker | Molecular Weight (g/mole) | Stokes Radius (Angstroms) | Diffusivity in Water 37 C. (cm$^2$/sec) |
| --- | --- | --- | --- |
| Glucose | 186 | ~3.5 | $9.24 \times 10^{-6}$ |
| Vitamin B12 | 1,300 | ~7.7 | $5.00 \times 10^{-6}$ |
| Cytochrome C | 13,400 | 16.5 | $1.78 \times 10^{-6}$ |
| Myoglobin | 16,900 | 15.2 | $1.57 \times 10^{-6}$ |
| α-chymotrypsinogen | 24,500 | 22.5 | $1.44 \times 10^{-6}$ |
| Ovalbumin | 43,500 | 27.6 | $1.02 \times 10^{-6}$ |
| BSA | 67,000 | 36.1 | $9.64 \times 10^{-7}$ |
| IgG | 155,000 | 51.3 | $6.29 \times 10^{-7}$ |
| Apoferritin | 440,000 | 59.3 | $6.11 \times 10^{-7}$ |
| Parvovirus |  | ~180 | $~2.4 \times 10^{-7}$ |
| Orthomyxoviridae |  | ~1200 | $~3.8 \times 10^{-8}$ |

As the nMWCO of a membrane increases from the ultrafiltration to the microporous range, the probability of virus passing through the membrane as a result of a concentration driving force increases. This ability to pass through a membrane is a function of the characteristic size of the viral particle and of the viral shape. FIG. 1 shows the log-order reduction in phage diffusion across two membranes of different nMWCOs. The ultrafiltration grade PAN/PVC membrane with a nMWCO of 100 kD (0.002 μm) is completely permeable to particles up to 440 kD when left over a 2 week period of time. Nevertheless, this membrane provides a 9 log-order reduction to the passage of phiX174 phage (~23 nm) over 2 weeks. This increases to a 12 log-order reduction for lambda GF10 (head 95 nm×65 nm; tail 115 nm×17 nm) even after 6 weeks. When the nMWCO of the membrane is increased into the microporous range—a polysulfone membrane with a 0.1 μm cutoff—the log-order reduction of phiX174 is eliminated over a 3 day period of time and lambda GT10 is reduced to a 6 log-order reduction at 6 weeks.

In addition to overall size, the shape of the virus is important in determining passage through the membrane. Phage M13 (5 nm×200 nm) was completely blocked by the ultrafiltration membrane (log-order reduction 14 after 2 weeks). It is hypothesized that some configurations of virus such as long flexible viral particles may become entangled within the membrane pores contributing to a higher log-order reduction than size alone would account for. Proper matching of membrane properties with particular virus properties, particularly size, shape, and flexibility, will allow for selective retention of viral sized particles.

Convective MWCO data for a range of particle sizes (proteins and dextrans) is used to characterize the fiber pore size. The MWCO of each fiber batch can be measured on a bundle of fibers potted in a cartridge. The cartridge is a hollow tube-like structure having capped ends. The fibers are threaded through the caps and sealed at the ends. The protein MWCO test involves ultrafiltering a protein solution (bovine serum albumin, Immunoglobulin G, myoglobin) at 5 pounds per square inch gauge (psig) transmembrane pressure. The reservoir and filtrate protein concentrations are measured on a spectrophotometer and the rejection coefficient (R) is calculated from their ratio as $R=1-Cf/Cr$, where Cf is the filtrate concentration and Cr is the reservoir concentration.

The convective dextran MWCO test differs from the diffusive protein MWCO test by controlling the filtrate volumetric flow rate in addition to controlling the retentate volumetric flow rate. The dextran test reagent is a polydisperse solution varying in molecular weight from 2,000 g/mole up to 4,000,000 g/mol (from Pharmacia). Dextran concentration across a range of molecular weights is measured both in the reservoir and in the filtrate with gel permeation chromatography. Rejection coefficients as a function of dextran radius are then calculated from the ratios of filtrate to reservoir concentrations. Either the full rejection profile can be reported or the dextran radii at 20%, 50%, and 90% rejection.

In addition to cell therapy uses, permselective macrocapsules can also be used to hold polymeric implants such as bioerodible polymers containing therapeutically useful substances. Such implants without a carrier may become brittle or fragile. Without a capsule carrier they may be difficult to retrieve after being implanted. As erodible polymers break down and release their target products, they may also become dislodged and may move into unintended sites. Microporous macrocapsules add the additional benefits of safety, retrievability, and tissue biocompatibility to polymeric delivery systems.

In order that the invention described herein may be more fully understood, the following examples are set forth. It should be understood that these examples are for illustrative purposes only and are not to be construed as limiting the scope of the invention in any manner.

EXAMPLE 1

Implantation of Allogeneic Fetal Brain Tissue

Microporous fibers were prepared by extruding a 10% polyethylene oxide (MW=100K), 10% PAN/PVC (MW=100K), 80% Dimethyl formamide (w/w) solution through the outer lumen of a coaxial extrusion nozzle. Water was used as a coagulant and was coextruded with the polymer through the center bore of the nozzle. Nominal MWCO of these fibers was 2,000 kD. The fiber had an inner diameter of 0.8 mm and an outer diameter of 1 mm.

Fetal brain tissue was prepared according to the method of Tresco, et al., *Society for Neuroscience Abstracts*, 18:393.2

(1992). Tissue was loaded into these fibers in the presence of Matrigel (Collaborative Research) as a growth substratum and implanted in the striatum of healthy adult male Sprague Dawley rats within three hours of tissue isolation. Rats were sacrificed at 2 (n=3) and 4 (n=4) weeks, and the implants were histologically analyzed. After two and four weeks, viable cells were present that displayed morphological phenotypes similar to cultures maintained in vitro and isolated at the same time. Some of the cells stained positive for tyrosine hydroxylase, indicating neuronal survival in vivo for at least four weeks.

EXAMPLE 2

Preparation of Macrocapsules Using

Low Molecular Weight Additives

The following casting solutions were prepared for hollow fibers: Solution 1 contained 12.5% PAN/PVC, 50.0% polyethylene glycol (MW 200) (PEG-200) and 37.5% N-methyl pyrrolidone (NMP). PEG-200 is a low molecular weight additive in which the PAN/PVC is not soluble. At room temperature, the solution is a homogeneous gel. The casting solution is heated to 50° C. and phase inverted into a bath at ambient temperature. A polymer results in which the nMWCO is approximately 120 kD. The hollow fiber resulting from a solution without the PEG-200 additive has a nMWCO of about 80 kD.

Solution 2 contains 13% PAN/PVC, 15% glycerol and NMP. It is a solid at room temperature and is spun fabricated in the manner described above. Membranes with nMWCOs ranging from approximately 200 kD to the microporous region, to even cell-permeable, may be fabricated.

EXAMPLE 3

Preparation of Macrocapsules Using Solvent

Addition in the Bore and Bath

A 12.5% PAN/PVC, 87.5% NMP solution is prepared. When this solution is coagulated in water, a standard ultrafiltration membrane results. When the same solution is precipitated in a solvent/water mixture, the MWCO increases greatly to the very high end of the ultrafiltration range (200 kD).

EXAMPLE 4

Retrieval of Immunoisolated Cells

Alginate Noodles

A sterile suspension of pancreatic islets was prepared from human pancreases by the method of Scharp et al., U.S. Pat. No. 4,868,121. A 2% solution of sodium alginate in physiological saline (PS; 150 mM NaCl) was prepared under sterile conditions, which was then diluted 1:1 with the prepared cells, for a final concentration of 1% alginate in the islet suspension.

1.0 mm cylindrical "noodles" of alginate (1.0% w/alginate, Pronova$^R$)—containing human pancreatic islets surrounded by a cell-free perimeter region were prepared as follows. The islet suspension was loaded into the inner chamber of a nested dual-bore coextrusion device of the configuration described in copending U.S. Pat. application Ser. No. 07/461,999, the inner bore of which has a diameter of 500 microns and the peripheral bore of which has a diameter of 600 microns. The outer chamber of this device was loaded with a solution of sterile 1% sodium alginate in PS.

The tip of the nozzle was immersed in a bath containing a sterile solution of 1% $CaCl_2$ in PS, which induces the hardening or gelling of alginate by cross-linkage of alginate polyions. The materials loaded into the chambers were coextruded into this bath, generating a continuously forming alginate cylinder containing a core region of alginate matrix-immobilized islets and a surrounding region of alginate matrix free of islets. The outer diameter of the jacket was 1.2 mm. The inner diameter of the core was 1.0–1.05 mm. The total islet volume of the core was 0.8 mm$^3$ (200 islets). The total core volume was 25.98 mm$^3$. The volume of the islets was 3% of the total core volume. The alginate of the core was cross-linked with the alginate of the jacket.

The relative thickness of the surrounding region was modified by adjusting the speeds at which the materials were extruded from the core and peripheral bores of the nozzle. In general as flow in the core increased, wall thickness decreased. As flow in the peripheral bore was increased wall thickness increased. Ranges of flow rates used were the same for both the core and periphery (0.3–1.5 ml/min.). The ends of the cylinder were sealed by dipping the cylinder first in a sterile 2% sodium alginate bath, then in a sterile 1% $CaCl_2$ bath. The macrocapsules so formed was maintained in sterile tissue culture medium prior to implantation.

These islet-containing "noodles" are cut to 2 cm. lengths using a sterile scalpel and loaded into 1.5 mm inner diameter PEO/PAN/PVC capsules and implanted subcutaneously into diabetic recipients.

Following 4 weeks, capsules are retrieved and islets assayed for viability.

EXAMPLE 5

Retrieval of Immunoisolated Cells

Microspheres

Microspheres containing living cells are prepared by two separate methods. Thermoplastic microspheres containing PC12 cells are prepared according to the method of Sefton U.S. Pat. No. 4,353,888. Alginate:polylysine microspheres are prepared according to the method of Lim U.S. Pat. No. 4,352,883. In both instances, the microspheres are of a diameter no greater than 500 µm. Microspheres are loaded into the thermoplastic restraining devices described in Example 1. All devices are tested to have nominal MWCOs of greater than 200 kD.

The PC12 containing macrocapsules are implanted into rat striata and left for 2 weeks. The macrocapsules are recovered, inspected for evidence of fibromatous overgrowth and assessed for cell viability.

EXAMPLE 6

Implantation of Adrenal Chromaffin Cells

Human adrenal chromaffin cells are prepared from human cadavers by the method of Sagen, U.S. Pat. No. 4,753,635, and placed in permselective macrocapsules prepared as described in Example 1.

Capsules are implanted intrathecally into the lumbar regions of human patients suffering from chronic pain. Following three weeks capsules are removed and found to be intact and containing viable cells.

EXAMPLE 7

Bacteriophage Retentivity Testing

A test was developed to measure the transport retardation of lambda gt10 provided by a PAN/PVC membrane. This phage was chosen to serve as a model system to predict flux retardation for encapsulation of similarly-sized or larger animal viruses. Three different fibers were studied as shown in Table 4:

TABLE 4

| Type of Membrane | Material | Pore Size (m) | Skin | Inner Diameter (mm) | Wall thickness (mm) |
|---|---|---|---|---|---|
| ultrafiltration | PAN/PVC | ~0.01[a] | double | 0.779 | 0.097 |
| ultrafiltration | PAN/PVC | ~0.01[a] | single | 0.682 | 0.086 |
| microporous | polysulfone | 0.2 | none | 0.948 | 0.029 |

[a]corresponds to a nominal MWCO of 100 kD.

Lambda gt10 phage stocks were grown on lawns of NM514 (*E. coli* from ATCC). Selected plates were reconstituted with 5 ml SM buffer (prepared using the methods of Sambrook J. et al., supra). These plates were gently shaken for 4 hours, the liquid pipetted into a centrifuge tube and 100 μl chloroform was added. After incubating for an hour, the stock was spun down at 3700 RPM and the supernatant recovered. Phage titer was determined prior to fiber loading.

NM514 were grown in NZCYM media supplemented with 0.2% maltose to an optical density (OD) of 2. After the OD was established, bacteria were spun down at 3700 RPM and resuspended in 10 mM $MgSO_4$ (made in sterile water) using 37° C. shaker bath until the pellet was fully suspended.

The testing device consisted of a 12 cm long cartridge with an internal volume of 9 ml filled with SM medium (FIG. 2). Two or three fibers were potted into the male taper luers of the testing cartridge using 5-minute epoxy. After potting the fibers into the devices, they were deglycerinated by ultrafiltration with Milli-Q water (100x fiber volume). The PAN/PVC fibers were conditioned by ultrafiltering HL1 media at 2x the fiber volume through the fibers. This treatment simulates the loading conditions used for encapsulating cells. Pore size of the membranes is decreased by protein adsorption to the membrane surface. In contrast, unconditioned polysulfone, microporous fibers were used to evaluate the increase in phage diffusion with increased membrane pore size. Loading the fiber with bacteriophage was accomplished by injecting 0.1 ml of bacteriophage stock into the fiber lumens through the luer using a 1 ml disposable syringe.

After potting and conditioning the fibers, the cartridge baths were replaced with fresh SM buffer. Fibers were then loaded and the fiber ends were capped and the devices placed in a 37° C. incubator. Baths were sampled at 1, 3 and 6 weeks and assayed for bacteriophage concentration using standard plaquing procedures.

RESULTS

Table 5 shows the phage concentration and $D_{membrane}$ at time 0 and 6 weeks.

TABLE 5

Distribution of Lambda gt10

| Treatment | cartridge | Phage Concentration (pfu/ml) | | | $D_{membrane}$ |
|---|---|---|---|---|---|
| | | 0 weeks lumen | 6 weeks lumen | 6 weeks bath | |
| PAN/PVC double skin HL 1 conditioned | 1 | 1.0e15 | 2.0e11 | 10 | $7 \times 10^{-23}$ |
| | 2 | 1.0e15 | 2.0e9 | 10 | $7 \times 10^{-23}$ |
| PAN/PVC single | 1 | 1.0e15 | 2e10 | 10 | $7 \times 10^{-23}$ |

TABLE 5-continued

Distribution of Lambda gt10

| Treatment | cartridge | Phage Concentration (pfu/ml) | | | $D_{membrane}$ |
|---|---|---|---|---|---|
| | | 0 weeks lumen | 6 weeks lumen | 6 weeks bath | |
| skin HL1 conditioned | 2 | 1.0e15 | 3e9 | 1e3 | $8 \times 10^{-21}$ |
| | 3 | 1.0e15 | 2e11 | 4e5 | $3 \times 10^{-16}$ |
| Polysulfone not conditioned | 1 | 1.0e15 | 6e10 | 7e7 | $5 \times 10^{-16}$ |
| | 2 | 1.0e15 | 5e10 | 5e7 | $3.8 \times 10^{-16}$ |
| | 3 | 1.0e15 | 1e10 | 8e7 | $6 \times 10^{-16}$ |

As seen by the difference in the phage concentrations in the lumen and the bath at 6 weeks, the membrane provided significant resistance for phage diffusion into the bath. There was a decrease in the total phage activity after 6 weeks of encapsulation. Controls indicated that phage stock held at 37° C. at high ($1 \times 10^{15}$ pfu/ml) and low ($1 \times 10^3$ pfu/ml) are stable after 6 weeks. If the phage adsorbed to the membrane surfaces, this could account for the measured decrease in activity over the 6 weeks. Consequently, phage retention at 6 weeks was calculated in two ways: (A) the total amount of phage loaded into the capsules was divided by the total phage concentration in the bath at 6 weeks or (B) the total amount of phage present in the lumen of the capsule at 6 weeks was divided by the phage concentration in the bath at 6 weeks. These calculated log-order reductions in phage diffusion is shown in Table 6.

TABLE 6

Log-order Reduction in Phage Diffusion[a]

| Treatment | Cartridge | Log Order Reduction | |
|---|---|---|---|
| | | Method A | Method B |
| PAN/PVC double skin HL1 conditioned | 1 | 9 | 12 |
| | 2 | 7 | 12 |
| PAN/PVC single skin HL1 conditioned | 1 | 7 | 10 |
| | 2 | 8 | 10 |
| | 3 | 6 | 12 |
| Polysulfone unconditioned | 1 | 3 | 8 |
| | 2 | 3 | 6 |
| | 3 | 3 | 6 |

[a]Method A log-order reduction = lumen conc at 6 wks/bath conc at 6 wks $$\text{Method B log order reduction} = \frac{\text{lumen conc at 0 wks} / 100}{\text{bath conc at 6 wks}}$$

Because the average dimensions for the lambda gt10 studied are 95x 65 nm for the head and 17x115 nm for the tail, the results of this experiment show that PAN/PVC membranes can retain adventitious agents larger than 95 nm by a factor of at least six orders of magnitude.

EXAMPLE 8

Phage Phi-X Retentivity Testing

The same types of membranes and methods of Example 7 were used to determine the transport retardation of phage phi-X. This phage is about 24–30 nm in diameter and is essentially spherical. The ultrafiltration PAN/PVC membrane was preconditioned with PC1 media, and the polysulfone microporous fiber was untreated. The samples were taken at 3 days for the microporous fiber and 1 and 2 weeks for the ultrafiltration fiber. LB broth (prepared using the methods of Sambrook J. et al., supra) was used in place of the SM media. The phi-x phage has a lower log order reduction at a shorter time than was seen for the larger lambda gt10 phage (Table 6 v. Table 5).

TABLE 7

Log-order Reduction in Phage Diffusion[a]

| Treatment | | Log Order Reduction | |
| --- | --- | --- | --- |
| Cartridge | Time | Method A | Method B |
| 1 | 2 weeks | 4 | 9 |
| 2 | 2 weeks | 7 | 10 |
| 3 | 1 week | 6 | 9 |
| 4 | 3 days | | 1 |
| 5 | 3 days | | 1 |
| 6 | 3 days | | 1 |

[a]Cartridges 1, 2, 3: PAN/PVC conditioned with PC1 media.
Cartridges 4, 5, 6: Polysulfone untreated fibers.

EXAMPLE 9

Protein Retentivity Testing

The fibers studied in Example 7 were further characterized by measurement of percent rejection for several standard proteins and a blend of polydisperse dextrans. The rejection for the proteins are shown in Table 8. The rejection for the polydisperse dextrans are shown in FIGS. 3 and 4.

TABLE 8

| Fiber | Protein | Rejection |
| --- | --- | --- |
| PAN/PVC double skin | Bovine Serum Albumin | 96.2% |
| HL1 conditioned | Ovalbumin | 60% |
| | Myoglobin | 26% |
| PAN/PVC single skin | Bovine Serum Albumin | 90% |
| HL1 conditioned | Ovalbumin | 79% |

All documents referred to herein are hereby expressly incorporated by reference.

What is claimed is:

1. An implantable permselective device for use in cell therapy comprising:
   (a) a core comprising living cells that are capable of secreting a selected biologically active product or of providing a selected biological function; and
   (b) an external jacket surrounding said core, said jacket comprising a biocompatible material substantially free of said cells, said jacket having a nominal molecular weight cutoff greater than about 440 kD; said core and said jacket forming a macrocapsule, which device is substantially non-immunoisolatory.

2. The permselective device of claim 1 wherein said core additionally comprises a hydrogel matrix, said living cells being immobilized by said matrix.

3. The permselective device of claim 1 wherein said biocompatible material is comprised of hydrogels.

4. The permselective device of claim 2 wherein said core and said biocompatible materials are comprised of the same hydrogel.

5. The permselective device of claim 1 wherein said biocompatible material comprises alginate cross-linked with a multivalent ion.

6. The permselective device of claim 1 wherein said biocompatible material comprises a thermoplastic membrane.

7. The permselective device of claim 1 wherein the said nominal molecular weight cutoff is between about 1,000 to about 3,000 kD.

8. The permselective device of claim 1 wherein said external jacket has a nominal molecular weight cutoff below the molecular weight of detrimental viruses which may be shed from said living cells.

9. The permselective device of claim 1 wherein said living cells have been genetically modified with a virus, and said nominal molecular weight cutoff is below the molecular weight of said virus.

10. The permselective device of claim 9 wherein said external jacket has a viral retentivity value of less than about $10^2$.

11. The permselective device of claim 1 further comprising:
   (c) a tether for the retrieval of said device.

12. The permselective device of claim 1 wherein said core additionally comprises immunoisolatory devices in which said living cells are encapsulated.

13. The permselective device of claim 12 wherein said immunoisolatory devices are selected from the group consisting of microspheres and alginate noodles.

14. An implantable device for providing a therapeutically useful product to a recipient, the device comprising:
   (a) a core comprising a polymeric implant that is capable of secreting a selected therapeutically useful product, and
   (b) an external jacket surrounding said core formed of a biocompatible material, said jacket having a nominal molecular weight cutoff greater than about 440 kD;
   said core and said jacket forming a macrocapsule, which macrocapsule is substantially non-immunoisolatory.

15. A method of cell therapy comprising implanting a permselective device into the body of a recipient, said device comprising:
   (a) a core comprising living cells that are capable of secreting a selected biologically active product or of providing a selected biological function; and
   (b) an external jacket surrounding said core, said jacket comprising a biocompatible material substantially free of said cells, said jacket having a nominal molecular weight cutoff greater than about 440 kD;
   said core and said jacket forming a macrocapsule, which macrocapsule is substantially non-immunoisolatory.

16. The method of claim 15 wherein said external jacket has a molecular weight cutoff below the molecular weight of detrimental viruses which may be shed from said living cells.

17. The method of claim 15 wherein said living cells have been genetically modified with a virus, and said nominal molecular weight cutoff is below the molecular weight of said virus.

18. The method of claim 17 wherein said external jacket has a Viral retentivity value of less than about $10^2$.

19. The method of claim 15 wherein said permselective device further comprises:
   (c) a tether for the retrieval of said macrocapsule, and said method comprises the additional step of retrieving said macrocapsule at the termination of said therapy.

* * * * *